United States Patent
Cosmescu

(10) Patent No.: US 11,246,651 B2
(45) Date of Patent: Feb. 15, 2022

(54) MONOPOLAR TELESCOPIC ELECTROSURGERY PENCIL WITH ARGON BEAM CAPABILITY

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 0 days.

(21) Appl. No.: 16/917,456

(22) Filed: Jun. 30, 2020

(65) Prior Publication Data

US 2020/0330155 A1    Oct. 22, 2020

Related U.S. Application Data

(62) Division of application No. 15/450,011, filed on Mar. 5, 2017, now Pat. No. 10,792,095.

(51) Int. Cl.

| | |
|---|---|
| *A61B 18/14* | (2006.01) |
| *A61B 18/04* | (2006.01) |
| *A61B 18/00* | (2006.01) |
| *A61B 18/12* | (2006.01) |

(52) U.S. Cl.
CPC ........ *A61B 18/1482* (2013.01); *A61B 18/042* (2013.01); *A61B 18/14* (2013.01); *A61B 18/1402* (2013.01); *A61B 2018/00071* (2013.01); *A61B 2018/00077* (2013.01); *A61B 2018/00083* (2013.01); *A61B 2018/00107* (2013.01); *A61B 2018/00184* (2013.01); *A61B 2018/00589* (2013.01); *A61B 2018/00601* (2013.01); *A61B 2018/1253* (2013.01); *A61B 2018/1412* (2013.01); *A61B 2218/008* (2013.01)

(58) Field of Classification Search
CPC ... A61B 18/042; A61B 18/14; A61B 18/1402; A61B 18/1482; A61B 2018/00071; A61B 2018/00077; A61B 2018/00083; A61B 2018/00107; A61B 2018/00184; A61B 2018/00589; A61B 2018/00601; A61B 2018/042; A61B 2018/1253; A61B 2218/008

See application file for complete search history.

(56) References Cited

U.S. PATENT DOCUMENTS

| | | |
|---|---|---|
| 4,674,498 A | 6/1987 | Stasz |
| 4,850,353 A | 7/1989 | Stasz et al. |
| 5,171,311 A | 12/1992 | Rydell et al. |
| 5,281,216 A | 1/1994 | Klicek |
| 2006/0025757 A1 | 2/2006 | Heim |
| 2010/0094283 A1 | 4/2010 | Cosmescu |
| 2013/0110108 A1 | 5/2013 | Davison et al. |
| 2014/0257273 A1 | 9/2014 | Cosmescu |
| 2015/0257817 A1 | 9/2015 | Zoran et al. |

FOREIGN PATENT DOCUMENTS

EP    0280798 B1    1/1993

OTHER PUBLICATIONS

International Search Report and the Written Opinion of the International Searching Authority from related PCT Application No. PCT/US2017/031137 dated Jul. 25, 2017.

*Primary Examiner* — Michael F Peffley
*Assistant Examiner* — Samantha M Good
(74) *Attorney, Agent, or Firm* — Zeman-Mullen & Ford, LLP

(57) ABSTRACT

A monopolar telescopic electrosurgery pencil with argon beam capabilities which includes telescoping members contained within the pencil and a monopolar electrosurgery blade assembly with a non-conductive tube member for an inert gas.

20 Claims, 6 Drawing Sheets

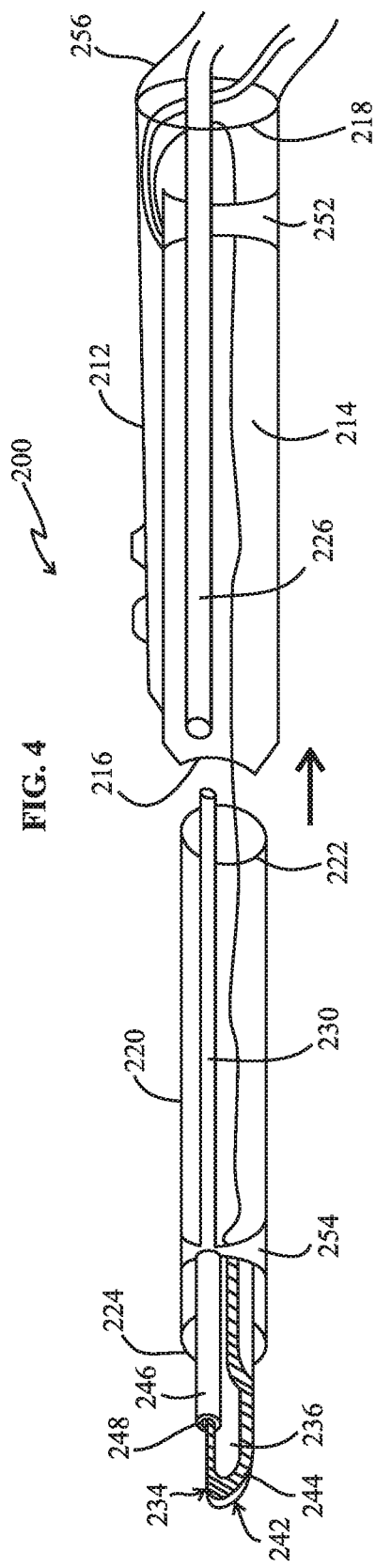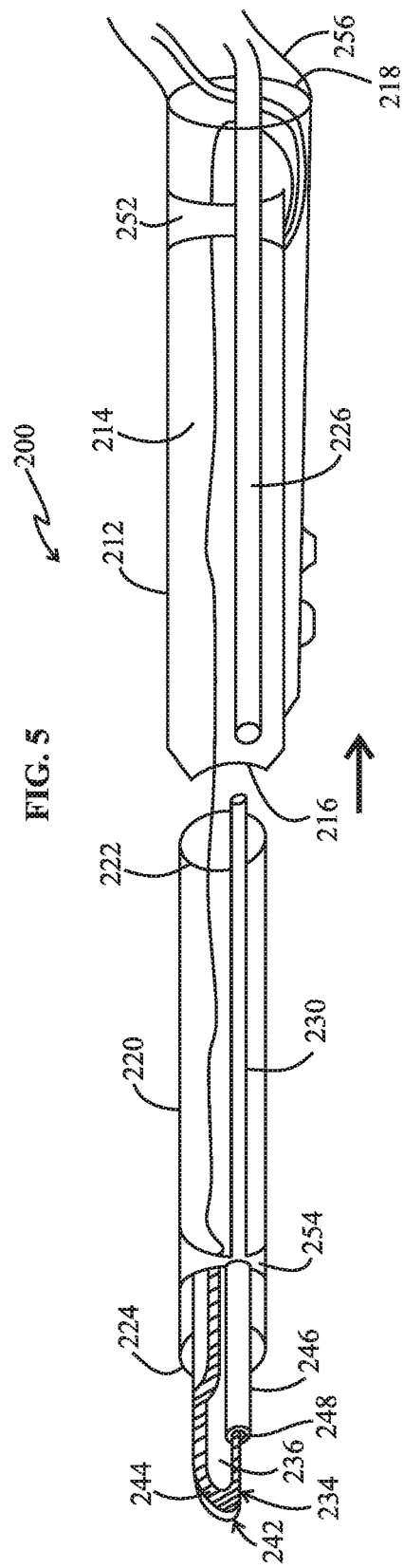

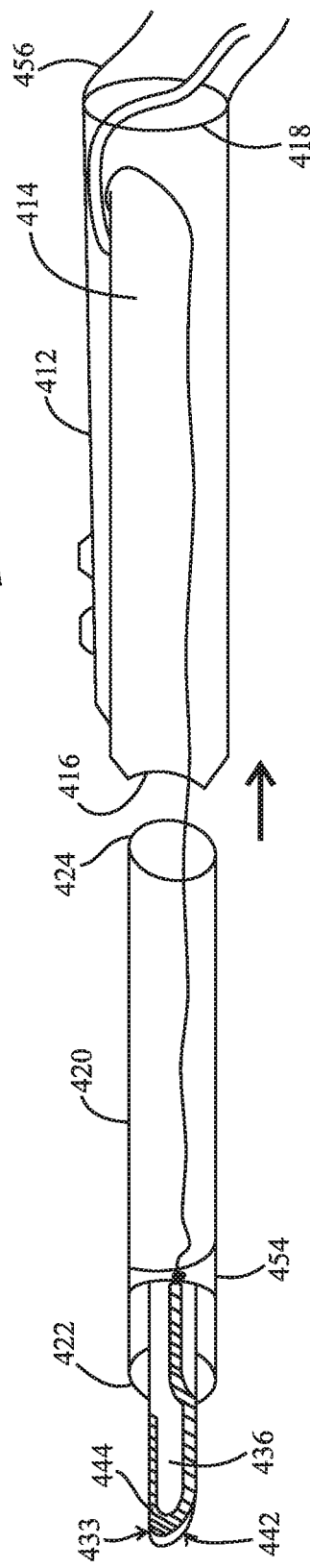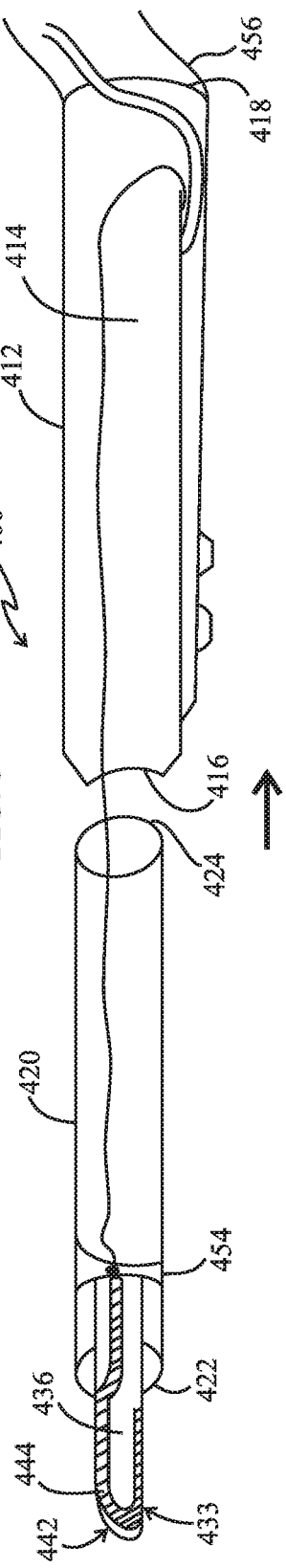

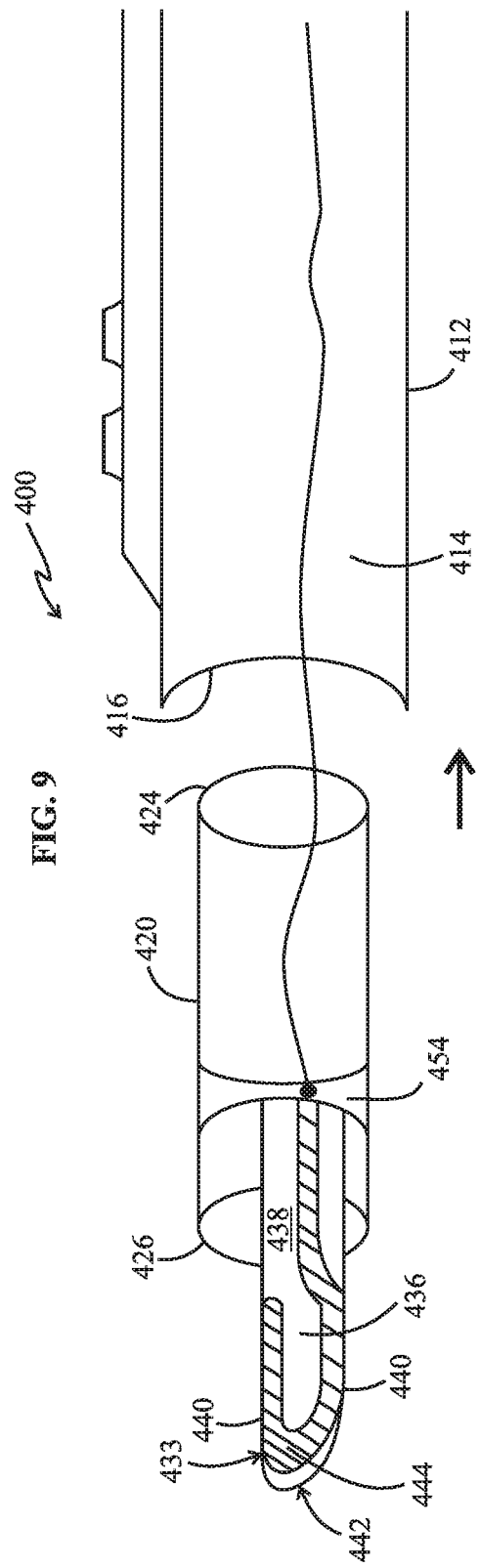

MONOPOLAR TELESCOPIC ELECTROSURGERY PENCIL WITH ARGON BEAM CAPABILITY

CROSS-REFERENCE TO RELATED APPLICATIONS

This application is a divisional of, and claims priority to, utility patent application having Ser. No. 15/450,011 filed Mar. 5, 2017, now U.S. Pat. No. 10,792,095, entitled "Monopolar Telescopic Electrosurgery Pencil With Argon Beam Capability" which is herein incorporated by reference in its entirety. This application is also related to patent application having Ser. No. 15/147,730, filed May 5, 2016, and provisional patent application having Ser. No. 62/362,968, filed Jul. 15, 2016, which are also herein incorporated by reference in their entireties.

FIELD OF THE INVENTION

The present invention is generally directed to electrosurgery blades including electrosurgery blades having argon beam capability. More particularly, the present invention relates to a monopolar telescopic electrosurgery pencil with argon beam capability which includes a handpiece member with a channel having first and second ends, a first non-conductive hollow tube contained within the channel and a conductive hollow tube contained within the channel, a hollow telescopic member having first and second ends where the second end of the hollow telescopic member is contained within the handpiece member, a second non-conductive hollow tube telescopically engaged with the first non-conductive hollow tube where the second non-conductive hollow tube is contained within the hollow telescopic member, a solid conductive cylindrical member contained within the hollow telescopic member and at least a portion of the conductive hollow tube, and an electrosurgery blade assembly positioned within the first end of the hollow telescopic member which includes a non-conductive planar member having opposing planar sides with opposing elongated edges and a sharp cutting end, a conductive layer located on at least one of the opposing planar sides where the conductive layer lies adjacent to at least one of the opposing elongated edges of the non-conductive planar member, and a non-conductive tube member having a hollow tubular shaped opening and a slot where the slot is positioned over at least a portion of the conductive layer and the second non-conductive hollow tube is connected to the non-conductive tube member.

BACKGROUND OF THE INVENTION

Typical electrosurgical pencils use an electrode blade which functions as an active electrode for use in performing cutting and coagulation during electrosurgery and a return electrode usually comprising an adhesive for attachment to a patient's skin. When the electrosurgery pencil is activated, the RF energy circulates from the active electrode to the return electrode through the patient's body with the distance between the active and return electrodes being fairly significant. Electrosurgery uses a RF generator and handpiece with an electrode to provide high frequency, alternating radio frequency (RF) current input at various voltages (2000-10,000V) depending on the function, namely coagulation vs. cutting. For cutting, heat generated from continuous RF high voltage conduction can create a vapor pocket which vaporizes and explodes a small section of tissue cells which results in an incision. Because of the heat generated, the lateral damage to the tissue is great and the possible necrosis of the tissue is high. For coagulation, voltage is usually lower than in cut mode and the slower heating process results in less heat. As a result, no vapor pocket is formed so the tissue for the most part remains intact but with cells and vessels destroyed and sealed at the point of contact.

It is also common to use argon beam coagulators during electrosurgery. In argon beam coagulation (ABC), plasma is applied to tissue by a directed beam of ionized argon gas (plasma) which causes a uniform and shallow coagulation surface thereby stopping blood loss. However, argon beam enhanced cutting may also be performed using application of an ionized argon gas.

At present, electrosurgery is often the best method for cutting and argon beam coagulation is often the best method for cessation of bleeding during surgery. Surgeons typically need to switch between argon beam coagulation and electrosurgery modes depending on what is happening during the surgery and what they need to achieve at a particular point in the surgery such as cutting, or making incisions in tissue, or stopping the bleeding at the surgical site.

However, since surgical tools and devices currently available to surgeons require switching between these two methods during the surgical procedure, there is a need for a surgical device or tool that enables a surgeon or user to utilize the best methods used for cutting and cessation of bleeding at the surgical site at the same time, or simultaneously, in addition to being able to use them separately. A monopolar telescopic electrosurgery pencil with argon beam capability having an electrosurgery blade with a sharp edge for cutting and RF and argon beam capability for capsulation would meet this need. The monopolar telescopic electrosurgery pencil described with reference to the present invention enables a user or surgeon to more easily and efficiently access the surgical site with enhanced viewing capability by extending the telescopic member of the pencil as well as the electrosurgery blade positioned within the telescopic member of the pencil. The monopolar telescopic electrosurgery pencil described with reference to the present invention also enables a user or surgeon to evacuate smoke and/or debris form the surgical site while being able to perform precise cutting at the surgical site as well as cutting and coagulation of tissue areas located at the surgical site.

Such a surgical device or tool would enable the surgeon or user to increase both the efficiency and accuracy of the surgery by enabling the surgeon or user to perform both tissue cutting and coagulation at the same time without switching between modes or methods thereby decreasing operating time and reducing or eliminating the lateral damage to the tissue. In addition, performing both tissue cutting and coagulation at the same time along with smoke evacuation would protect the surgeon and staff form inhaling smoke and particles and also enable the surgeon or user to more clearly view the surgical site to ensure accuracy during the procedure without the need to stop and switch modes in order to stop bleeding at the surgery site before being able to clearly see the surgical site.

SUMMARY OF THE INVENTION

The present invention is directed to a monopolar telescopic electrosurgery pencil with argon beam capability which includes a handpiece member with a channel having first and second ends, a first non-conductive hollow tube contained within the channel, a conductive hollow tube contained within the channel, a hollow telescopic member having first and second ends where the second end of the hollow telescopic member is contained within the handpiece member, a second non-conductive hollow tube telescopically engaged with the first non-conductive hollow tube wherein the second non-conductive hollow tube is contained within the hollow telescopic member, a solid conductive cylindrical member contained within the hollow telescopic member and at least a portion of the conductive hollow tube, and an electrosurgery blade assembly positioned within the first end of the hollow telescopic member which includes a non-conductive planar member having opposing planar sides with opposing elongated edges and a sharp cutting end, a conductive layer located on at least one of the opposing planar sides where the conductive layer lies adjacent to at least one of the opposing elongated edges of the non-conductive planar member, and a non-conductive tube member having a hollow tubular shaped opening and a slot where the slot is positioned over at least a portion of the conductive layer of the electrosurgery blade assembly and the second non-conductive hollow tube within the hollow telescopic member is connected to the non-conductive tube member of the electrosurgery blade assembly.

The monopolar telescopic electrosurgery pencil of the present invention may also include at least one support member for retaining the first non-conductive hollow tube and the conductive hollow tube within the channel of the handpiece member and at least one support member for retaining the second non-conductive hollow tube and the solid conductive cylindrical member within the hollow telescopic member. The monopolar telescopic electrosurgery pencil may also include a rotating member connected to the second end of the handpiece member. Further, the conductive hollow tube contained within the channel of the handpiece member may have an insulator covering its outer surface.

The conductive layer of the electrosurgery blade assembly in the monopolar telescopic electrosurgery pencil of the present invention may form a closed loop shaped portion located on one or more of the opposing planar sides of the non-conductive planar member. Further, where closed loop portions of the conductive layer are located on both opposite planar sides of the non-conductive planar member, they may further cover at least a portion of one of the opposing elongate planar sides of the non-conductive planar member so that the two closed loop portions on opposite sides of the non-conductive planar member are joined together.

The slot in the non-conductive tube member of the electrosurgery blade assembly may also be positioned over at least a portion of the non-conductive planar member and the hollow tubular shaped opening of the non-conductive tube member is preferably positioned so that an inert gas supplied through the hollow tubular shaped opening of the non-conductive tube member will come in contact with at least a portion of the conductive layer of the electrosurgery blade assembly. The non-conductive tube member of the electrosurgery blade assembly may comprise a ceramic and at least a portion of the non-conductive tube member may be positioned outside of the first end of the hollow telescopic member. In addition, the non-conductive planar member of the electrosurgery blade assembly may also comprise a ceramic.

In another exemplary embodiment, the monopolar telescopic electrosurgery pencil with argon beam capability of the present invention may include a handpiece member with a channel having first and second ends, a first non-conductive hollow tube contained within the channel, a hollow telescopic member having first and second ends with the second end contained within the handpiece member, a second non-conductive hollow tube telescopically engaged with the first non-conductive hollow tube with the second non-conductive hollow tube contained within the hollow telescopic member, and an electrosurgery blade assembly positioned within the first end of the hollow telescopic member which includes a non-conductive planar member having opposing planar sides with opposing elongated edges and a sharp cutting end, a conductive layer located on at least one of the opposing planar sides where the conductive layer lies adjacent to at least one of the opposing elongated edges of the non-conductive planar member, and a non-conductive tube member having a hollow tubular shaped opening and a slot where the slot is positioned over at least a portion of the conductive layer of the electrosurgery blade assembly and the second non-conductive hollow tube is connected to the non-conductive tube member. The monopolar telescopic electrosurgery pencil with argon beam capability may also include at least one support member for retaining the first non-conductive hollow tube within the channel of the handpiece member and at least one support member for retaining the second non-conductive hollow tube within the telescopic member. Further, the conductive layer of the electrosurgery blade assembly preferably covers at least a portion of at least one of the opposing elongated edges of the non-conductive planar member so that an inert gas supplied through the hollow tubular shaped opening of the non-conductive tube member will come into contact with at least a portion of the conductive layer.

Still another embodiment of the invention is directed to a monopolar telescopic electrosurgery pencil without argon beam capability which includes a handpiece member with a channel having first and second ends, a hollow telescopic member having first and second ends where the second end is contained in the handpiece member, an electrosurgery blade positioned within the first end of the hollow telescopic member which includes a non-conductive planar member having opposite planar sides with opposing elongated edges and a cutting tip, and a conductive layer located on at least one of the opposing planar sides where the conductive layer lies adjacent to at least one of the opposing elongated edges of the non-conductive planar member without covering at least a portion of the opposing planar side that lies adjacent to the cutting tip, and a support member for retaining the electrosurgery blade within the hollow telescopic member.

BRIEF DESCRIPTION OF THE DRAWINGS

The subject invention will hereinafter be described in conjunction with the appended drawing figures, wherein like numerals denote like elements.

FIG. 4 is a perspective view of a third exemplary embodiment of the monopolar telescopic electrosurgery pencil with argon beam capability of the present invention which shows the telescopic member disconnected from the handpiece member of the electrosurgery pencil and the interior elements of the electrosurgery pencil;

FIG. 5 is the same as the view shown in FIG. 4 but with the monopolar telescopic electrosurgery pencil with argon beam capability shown rotated 180 degrees;

FIG. 7 is a perspective view of an exemplary embodiment of a monopolar telescopic electrosurgery pencil without argon beam capability which shows the telescopic member disconnected from the handpiece member of the electrosurgery pencil and the interior elements of the electrosurgery pencil;

FIG. 8 is the same as the view shown in FIG. 7 but with the monopolar telescopic electrosurgery pencil without argon beam capability shown rotated 180 degrees; and FIG. 9 is an enlarged partial view of FIG. 7.

DETAILED DESCRIPTION OF EXEMPLARY EMBODIMENTS

Exemplary embodiments of the monopolar telescopic electrosurgery pencil with argon beam capability enable a user or surgeon to separately use a sharp edged electrode for cutting and/or coagulation, separately use an argon beam for cutting and/or coagulation, or simultaneously use a sharp edged electrode and an argon beam for cutting and/or coagulation. An exemplary embodiment of a monopolar telescopic electrosurgery pencil without argon beam capability is also presented which enables a user or surgeon to cut and/or coagulate tissue.

Figure 1:
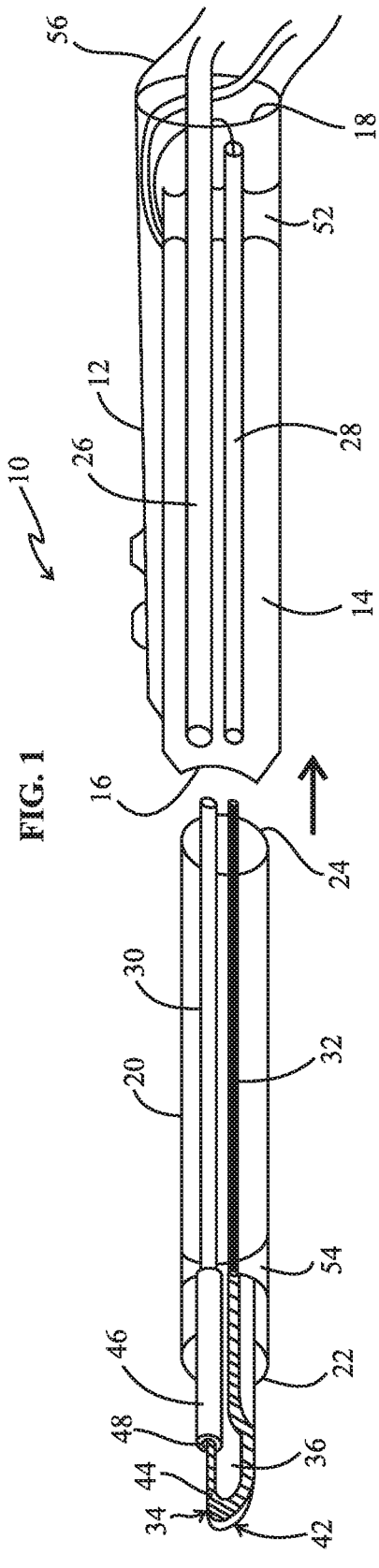
FIG. 1 is a perspective view of a first exemplary embodiment of the monopolar telescopic electrosurgery pencil with argon beam capability of the present invention which shows the telescopic member disconnected from the handpiece member of the electrosurgery pencil and the interior elements of the electrosurgery pencil.
Figure 2:
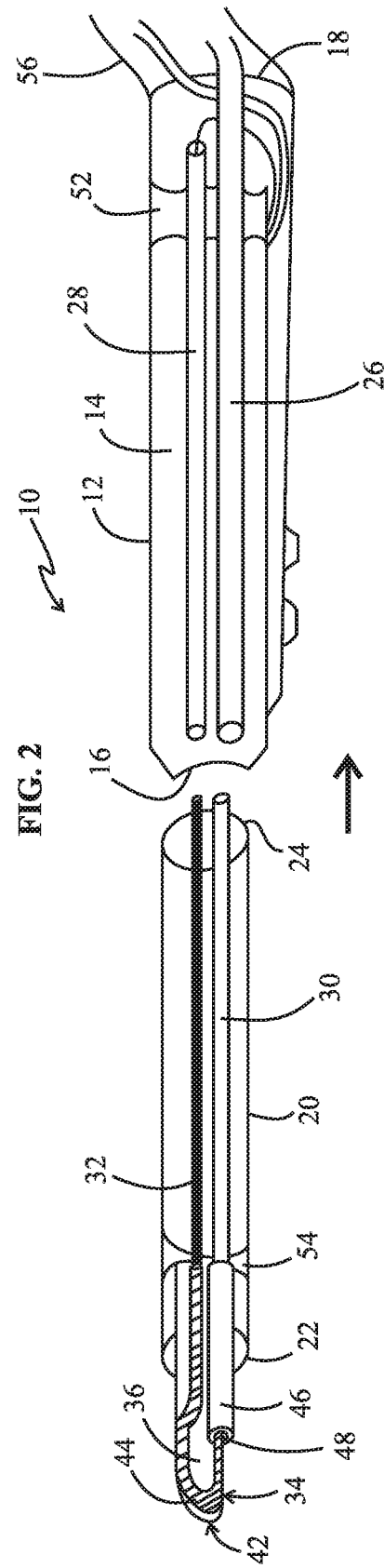
FIG. 2 is the same as the view shown in FIG. 1 but with the monopolar telescopic electrosurgery pencil with argon beam capability shown rotated 180 degrees.

FIGS. 1 and 2 show perspective views of a first exemplary embodiment of the monopolar telescopic electrosurgery pencil with argon beam capability 10 of the present invention which shows the telescopic member 20 disconnected from the handpiece member 12 of the electrosurgery pencil and the interior elements of the electrosurgery pencil 10. Monopolar electrosurgery pencil with argon beam capability 10 includes a handpiece member 12 with a channel 14 having first end 16 and second end 18 and a hollow telescopic member 20 having a first end 22 and a second end 24 where the second end 24 of the hollow telescopic member 20 is inserted into the first end 16 of handpiece member 12 so that it is contained within handpiece member 12 when the pencil 10 is in use. In order to make the monopolar telescopic electrosurgery pencil with argon beam capability 10 telescopic, a first non-conductive hollow tube member 26 and a conductive hollow tube member 28 are located within the handpiece member 12 and a second non-conductive hollow tube 30 and a solid conductive cylindrical member 32 are located in the hollow telescopic member 20 so that the first non-conductive hollow tube member 26 can telescopically engage with second non-conductive hollow tube member 30 and conductive hollow tube member 26 can telescopically engage with solid conductive cylindrical member 32. In the embodiment shown in FIGS. 1 and 2, the second non-conductive hollow tube 30 has a smaller diameter than the first non-conductive hollow tube 26 and fits within first non-conductive hollow tube 26 such that it is in slidable engagement with first non-conductive hollow tube 26. Further, solid conductive cylindrical member 32 has a smaller diameter than conductive hollow tube 28 and fits within conductive tube 28 such that it is in slidable engagement with conductive hollow tube 28.

The monopolar telescopic electrosurgery pencil with argon beam capability 10 also includes an electrosurgery blade assembly like those shown and described in Ser. No. 15/147,730, which is herein incorporated by reference in its entirety. Turning back to FIG. 1, monopolar telescopic electrosurgery pencil with argon beam capability 10 includes an electrosurgery blade assembly 34 positioned within the first end 22 of hollow telescopic member 20 that includes a non-conductive planar member 36 having opposing planar sides 38 with opposing elongated edges 40 and a sharp cutting end/tip 42, a conductive layer 44 located on at least one side of the opposing planar sides 38 with the conductive layer 44 lying adjacent to at least one of the opposing elongated edges 40 of the non-conductive planar member 36, and a non-conductive tube member 46 having a hollow tubular shaped opening 48 and a slot 50 where the slot 50 is positioned over at least a portion of the conductive layer 44 and the second non-conductive hollow tube 30 is connected to the non-conductive tube member 46. The electrosurgery blade assembly 34 is the same as the electrosurgery blade assembly 134 shown in FIG. 3 and therefore the components of the electrosurgery blade 34 can be better seen in FIG. 3.

Monopolar telescopic electrosurgery pencil with argon beam capability 10 may also include at least one support member 52 for retaining first non-conductive hollow tube 26 and conductive hollow tube 28 within the channel 14 of handpiece 12. Monopolar telescopic electrosurgery pencil with argon beam capability 10 may also include at least one support member 54 for retaining second non-conductive hollow tube 30 and solid conductive cylindrical member 32 within hollow telescopic member 20. Further, monopolar telescopic electrosurgery pencil with argon beam capability 10 may also include a rotating member 56 connected to the second end 18 of handpiece member 12 to eliminate or reduce drag on the electrosurgery pencil 10, as well as kinking of vacuum tubing (not shown) which is attached to the end of the pencil for smoke evacuation, while the electrosurgery pencil 10 is in use.

The hollow tubular shaped opening 48 in the non-conductive tube member 46 of the electrosurgery blade assembly 34 is positioned such that an inert gas, such as argon gas, supplied through the hollow tubular shaped opening 48 will come in contact with at least a portion of the conductive layer 44 of the electrosurgery blade assembly 34. In addition to being positioned over at least a portion of the conductive layer 44, the slot 50 in the non-conductive tube member 46 may also be positioned over at least a portion the opposing planar sides 38 of the non-conductive planar member 36. At least a portion of the non-conductive tube member 46 of the electrosurgery blade assembly 34 is preferably positioned outside of the first end 22 of the hollow telescopic member 20.

The conductive layer 44 of the electrosurgery blade assembly 34 may form a closed loop shaped portion located on one or both opposite planar sides 38 of the non-conductive planar member 36. In addition, when closed loop shaped portions of conductive layer 44 are located on both opposite planar sides 38 of non-conductive planar member 36, they may also cover a portion of the opposing elongated edges 40 of non-conductive planar member 36 so that the closed loop shaped portions are joined over atop of the non-conductive planar member 36. The non-conductive planar member 36 and the non-conductive tube member 46 of the electrosurgery blade assembly 34 may comprise a ceramic material. In addition, the conductive hollow tube 28 within the handpiece member 12 may have an insulator on its outer surface.

Figure 3:
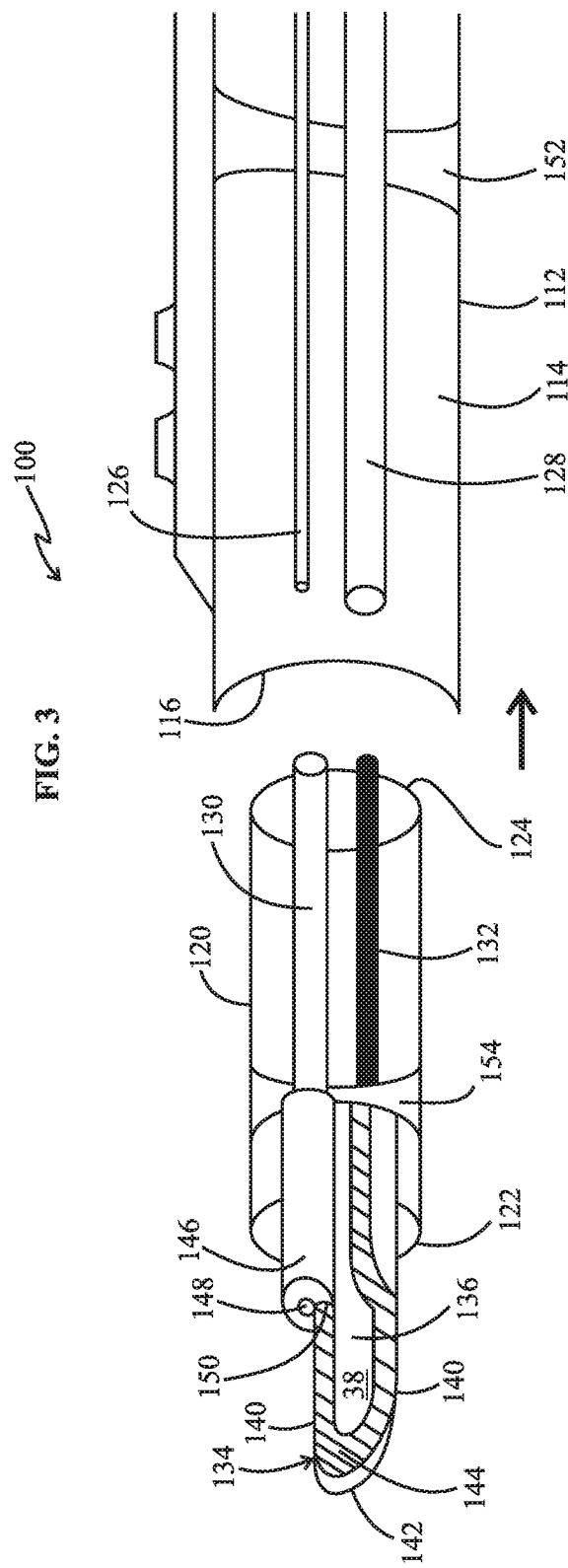
FIG. 3 is an enlarged partial perspective view of a second exemplary embodiment of the monopolar telescopic electrosurgery pencil with argon beam capability of the present invention which shows the telescopic member disconnected from the handpiece member of the electrosurgery pencil and the interior elements of the electrosurgery pencil.

FIG. 3 is an enlarged partial perspective view of a second exemplary embodiment of the monopolar telescopic electrosurgery pencil with argon beam capability 100 of the present invention which shows the telescopic member 120 disconnected from the handpiece member 112 of the electrosurgery pencil and the interior elements of the electrosurgery pencil. Like the embodiment shown in FIGS. 1 and 2, monopolar electrosurgery pencil with argon beam capability 100 includes a handpiece member 112 with a channel 114 having first end 116 and second end 118 and a hollow telescopic member 120 having a first end 122 and a second end 124 where the second end 124 of the hollow telescopic member 120 is inserted into the first end 116 of handpiece member 112 so that it is contained within handpiece member 112 when the pencil 110 is in use. In order to make the monopolar telescopic electrosurgery pencil with argon beam capability 110 telescopic, a first non-conductive hollow tube member 126 and a conductive hollow tube member 128 are located within the handpiece member 112 and a second non-conductive hollow tube 130 and a solid conductive cylindrical member 132 are located in the hollow telescopic member 120 so that the first non-conductive hollow tube member 126 can telescopically engage with second non-conductive hollow tube member 130 and conductive hollow tube member 126 can telescopically engage with solid conductive cylindrical member 132. However, in the embodiment shown in FIG. 3, the first non-conductive hollow tube 126 has a smaller diameter than the second non-conductive hollow tube 130 and fits within second non-conductive hollow tube 130 such that it is in slidable engagement with second non-conductive hollow tube 130. Solid conductive cylindrical member 132 is the same as in FIGS. 1 and 2 and has a smaller diameter than conductive hollow tube 128 and fits within conductive tube 128 such that it is in slidable engagement with conductive hollow tube 128.

The monopolar telescopic electrosurgery pencil with argon beam capability 100 also includes an electrosurgery blade assembly 134 like that shown in FIGS. 1 AND 2. The monopolar telescopic electrosurgery pencil with argon beam capability 100 includes an electrosurgery blade assembly 134 positioned within the first end 122 of hollow telescopic member 120 that includes a non-conductive planar member 136 having opposing planar sides 138 with opposing elongated edges 140 and a sharp cutting end/tip 142, a conductive layer 144 located on at least one side of the opposing planar sides 138 with the conductive layer 144 lying adjacent to at least one of the opposing elongated edges 140 of the non-conductive planar member 136, and a non-conductive tube member 146 having a hollow tubular shaped opening 148 and a slot 150 where the slot 150 is positioned over at least a portion of the conductive layer 144 and the second non-conductive hollow tube 130 is connected to the non-conductive tube member 146.

The hollow tubular shaped opening 148 in the non-conductive tube member 146 of the electrosurgery blade assembly 134 is positioned such that an inert gas, such as argon gas, supplied through the hollow tubular shaped opening 148 will come in contact with at least a portion of the conductive layer 144 of the electrosurgery blade assembly 134. In addition to being positioned over at least a portion of the conductive layer 144, the slot 150 in the non-conductive tube member 146 may also be positioned over at least a portion the opposing planar sides 138 of the non-conductive planar member 136. At least a portion of the non-conductive tube member 146 of the electrosurgery blade assembly 134 is preferably positioned outside of the first end 122 of the hollow telescopic member 120.

Like previously described with reference to FIGS. 1 and 2, the conductive layer 144 of the electrosurgery blade assembly 134 shown in FIG. 3 may form a closed loop shaped portion located on one or both opposite planar sides 138 of the non-conductive planar member 136. In addition, when closed loop shaped portions of conductive layer 144 are located on both opposite planar sides 138 of non-conductive planar member 136, they may also cover a portion of the opposing elongated edges 140 of non-conductive planar member 136 so that the closed loop shaped portions are joined over a top of the non-conductive planar member 136. The non-conductive planar member 136 and the non-conductive tube member 146 of the electrosurgery blade assembly 134 may comprise a ceramic material. In addition, the conductive hollow tube 128 within the handpiece member 112 may have an insulator on its outer surface.

Monopolar telescopic electrosurgery pencil with argon beam capability 100 may also include at least one support member 152 for retaining first non-conductive hollow tube 126 and conductive hollow tube 128 within the channel 114 of handpiece 112. Monopolar telescopic electrosurgery pencil with argon beam capability 100 may also include at least one support member 154 for retaining second non-conductive hollow tube 130 and solid conductive cylindrical member 132 within hollow telescopic member 120. Non-conductive tube member 146 of electrosurgery blade assembly 134 may be seated in support member 154. Alternatively, second non-conductive hollow tube 130 may be seated in support member 154 so that electrosurgery blade assembly 134 forms a separate detachable unit that can be removed from support member 154 and reattached to support member 154. Further, monopolar telescopic electrosurgery pencil with argon beam capability 100 may also include a rotating member 156 connected to the second end 118 of handpiece member 112 to eliminate or reduce drag on the electrosurgery pencil 100, as well as kinking of vacuum tubing (not shown) which is attached to the end of the pencil for smoke evacuation, while the electrosurgery pencil 100 is in use.

FIGS. 4 and 5 show perspective views of a third exemplary embodiment of the monopolar telescopic electrosurgery pencil with argon beam capability 200 of the present invention which shows the telescopic member 220 disconnected from the handpiece member 212 of the electrosurgery pencil 200 and the interior elements of the electrosurgery pencil 200. The monopolar telescopic electrosurgery pencil with argon beam capability 200 includes a handpiece member 212 with a channel 214 having first and second ends 216, 218, a first non-conductive hollow tube 226 contained within the channel 214, a hollow telescopic member 220 having first and second ends 222, 224 with the second end 224 contained within the handpiece member 212, a second non-conductive hollow tube 230 telescopically engaged with the first non-conductive hollow tube 226 with the second non-conductive hollow tube 230 contained within the hollow telescopic member 220, and an electrosurgery blade assembly 234 positioned within the first end 222 of the hollow telescopic member 220 which includes a non-conductive planar member 236 having opposing planar sides 238 with opposing elongated edges 240 and a sharp cutting end 242, a conductive layer 244 located on at least one of the opposing planar sides 238 where the conductive layer 244 lies adjacent to at least one of the opposing elongated edges 240 of the non-conductive planar member 236, and a non-conductive tube member 246 having a hollow tubular shaped opening 248 and a slot 250 where the slot 250 is positioned over at least a portion of the conductive layer 244 of the electrosurgery blade assembly 234 and the second non-conductive hollow tube 230 is connected to the non-conductive tube member 246. The monopolar telescopic electrosurgery pencil with argon beam capability 200 may also include at least one support member 252 for retaining the first non-conductive hollow tube 226 within the channel 214 of the handpiece member 212 and at least one support member 254 for retaining the second non-conductive hollow tube 230 within the hollow telescopic member 220. Further, the conductive layer 244 of the electrosurgery blade assembly 234 preferably covers at least a portion of at least one of the opposing elongated edges 240 of the non-conductive planar member 236 so that an inert gas supplied through the hollow tubular shaped opening 248 of the non-conductive tube member 246 will come into contact with at least a portion of the conductive layer 244.

In addition to being positioned over at least a portion of the conductive layer 244, the slot 250 in the non-conductive tube member 246 may also be positioned over at least a portion the opposing planar sides 238 of the non-conductive planar member 236. At least a portion of the non-conductive tube member 246 of the electrosurgery blade assembly 234 is preferably positioned outside of the first end 222 of the hollow telescopic member 220. The conductive layer 244 of the electrosurgery blade assembly 234 may form a closed loop shaped portion located on one or both opposite planar sides 238 of the non-conductive planar member 236. In addition, when closed loop shaped portions of conductive layer 244 are located on both opposite planar sides 238 of non-conductive planar member 236, they may also cover a portion of the opposing elongated edges 240 of non-conductive planar member 236 so that the closed loop shaped portions are joined over a top of the non-conductive planar member 236. The non-conductive planar member 236 and the non-conductive tube member 46 of the electrosurgery blade assembly 234 may comprise a ceramic material.

In order to make the monopolar telescopic electrosurgery pencil with argon beam capability 200 telescopic, the second end 224 of the hollow telescopic member 220 is inserted into the first end 216 of handpiece member 212 so that it is contained within handpiece member 212 when the pencil 210 is in use. Further, first non-conductive hollow tube member 226 is located within handpiece member 212 and second non-conductive hollow tube 230 is located in hollow telescopic member 220 so that the first non-conductive hollow tube member 226 can telescopically engage with second non-conductive hollow tube member 230. In the embodiment shown in FIGS. 4 and 4, the second non-conductive hollow tube 230 has a smaller diameter than the first non-conductive hollow tube 226 and fits within first non-conductive hollow tube 226 such that it is in slidable engagement with first non-conductive hollow tube 226.

Monopolar telescopic electrosurgery pencil with argon beam capability 200 may also include a rotating member 256 connected to the second end 218 of handpiece member 212 to eliminate or reduce drag on the electrosurgery pencil 200, as well as kinking of vacuum tubing (not shown) which is attached to the end of the pencil for smoke evacuation, while the electrosurgery pencil 200 is in use.

Figure 6:
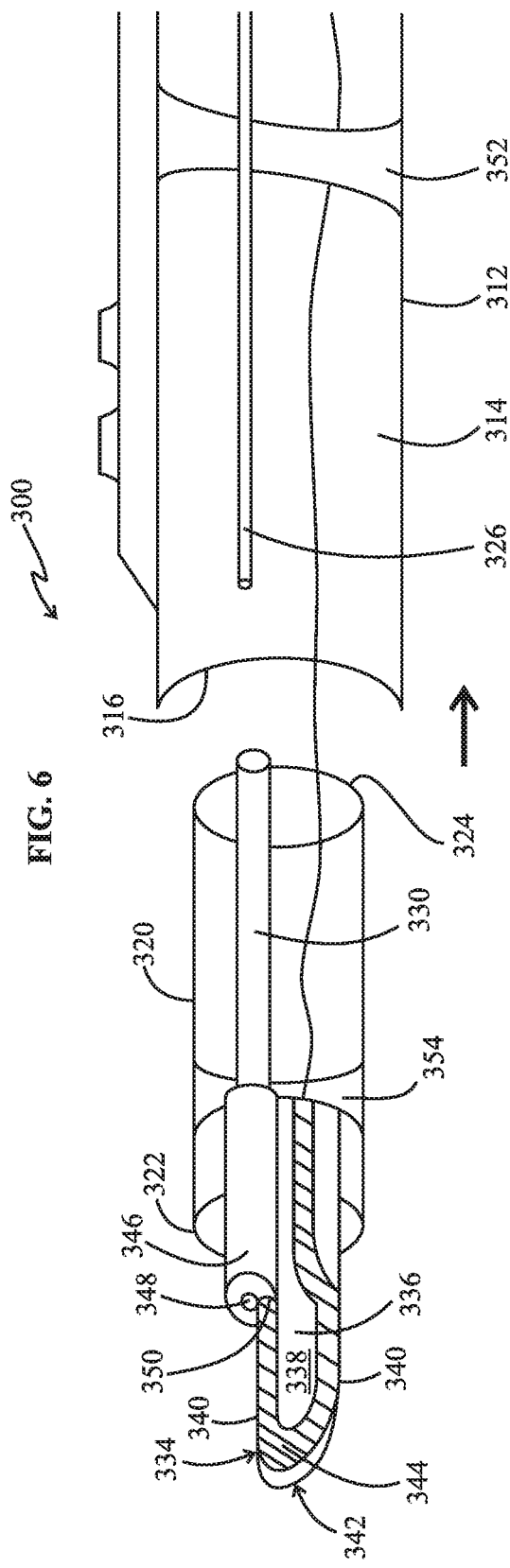
FIG. 6 is an enlarged partial view of a fourth exemplary embodiment of the monopolar telescopic electrosurgery pencil with argon beam capability of the present invention which shows the telescopic member disconnected from the handpiece member of the electrosurgery pencil and the interior elements of the electrosurgery pencil.

FIG. 6 is an enlarged partial view of a fourth exemplary embodiment of the monopolar telescopic electrosurgery pencil with argon beam capability 300 of the present invention which shows the telescopic member 320 disconnected from the handpiece member 312 of the electrosurgery pencil 300 and the interior elements of the electrosurgery pencil 300. Like the embodiment shown in FIGS. 4 and 5, monopolar electrosurgery pencil with argon beam capability 300 includes a handpiece member 312 with a channel 314 having first end 316 and second end 318 and a hollow telescopic member 320 having a first end 322 and a second end 324 where the second end 324 of the hollow telescopic member 320 is inserted into the first end 316 of handpiece member 312 so that it is contained within handpiece member 312 when the pencil 300 is in use. In order to make the monopolar telescopic electrosurgery pencil with argon beam capability 300 telescopic, a first non-conductive hollow tube member 326 is located within the handpiece member 312 and a second non-conductive hollow tube 330 is located in the hollow telescopic member 320 so that the first non-conductive hollow tube member 326 can telescopically engage with second non-conductive hollow tube member 330. However, in the embodiment shown in FIG. 6, the first non-conductive hollow tube 326 has a smaller diameter than the second non-conductive hollow tube 330 and fits within second non-conductive hollow tube 330 such that it is in slidable engagement with second non-conductive hollow tube 330.

The monopolar telescopic electrosurgery pencil with argon beam capability 300 also includes an electrosurgery blade assembly 334 like that shown in FIGS. 4 and 5. The monopolar telescopic electrosurgery pencil with argon beam capability 300 includes an electrosurgery blade assembly 334 positioned within the first end 322 of hollow telescopic member 320 that includes a non-conductive planar member 336 having opposing planar sides 338 with opposing elongated edges 340 and a sharp cutting end/tip 342, a conductive layer 344 located on at least one side of the opposing planar sides 338 with the conductive layer 344 lying adjacent to at least one of the opposing elongated edges 340 of the non-conductive planar member 336, and a non-conductive tube member 346 having a hollow tubular shaped opening 348 and a slot 350 where the slot 350 is positioned over at least a portion of the conductive layer 344 and the second non-conductive hollow tube 330 is connected to the non-conductive tube member 346.

The hollow tubular shaped opening 348 in the non-conductive tube member 346 of the electrosurgery blade assembly 334 is positioned such that an inert gas, such as argon gas, supplied through the hollow tubular shaped opening 348 will come in contact with at least a portion of the conductive layer 344 of the electrosurgery blade assembly 334. In addition to being positioned over at least a portion of the conductive layer 344, the slot 350 in the non-conductive tube member 346 may also be positioned over at least a portion the opposing planar sides 338 of the non-conductive planar member 336. At least a portion of the non-conductive tube member 346 of the electrosurgery blade assembly 334 is preferably positioned outside of the first end 322 of the hollow telescopic member 320.

Like previously described with reference to FIGS. 4 and 5, the conductive layer 344 of the electrosurgery blade assembly 334 shown in FIG. 6 may form a closed loop shaped portion located on one or both opposite planar sides 338 of the non-conductive planar member 336. In addition, when closed loop shaped portions of conductive layer 344 are located on both opposite planar sides 338 of non-conductive planar member 336, they may also cover a portion of the opposing elongated edges 340 of non-conductive planar member 336 so that the closed loop shaped portions are joined over a top of the non-conductive planar member 336. The non-conductive planar member 336 and the non-conductive tube member 346 of the electrosurgery blade assembly 334 may comprise a ceramic material. In addition, the conductive hollow tube 328 within the handpiece member 312 may have an insulator on its outer surface.

Monopolar telescopic electrosurgery pencil with argon beam capability 300 may also include at least one support member 352 for retaining first non-conductive hollow tube 326 within the channel 314 of handpiece 312. Monopolar telescopic electrosurgery pencil with argon beam capability 300 may also include at least one support member 354 for retaining second non-conductive hollow tube 330 within hollow telescopic member 320. Non-conductive tube member 346 of electrosurgery blade assembly 334 may be seated in support member 354. Alternatively, second non-conductive hollow tube 330 may be seated in support member 354 so that electrosurgery blade assembly 334 forms a separate detachable unit that can be removed from support member 354 and reattached to support member 354. Further, monopolar telescopic electrosurgery pencil with argon beam capability 300 may also include a rotating member 356 connected to the second end 318 of handpiece member 312 to eliminate or reduce drag on the electrosurgery pencil 300, as well as kinking of vacuum tubing (not shown) which is attached to the end of the pencil for smoke evacuation, while the electrosurgery pencil 300 is in use.

As can be seen in previously described FIGS. 1-6, the hollow tubular shaped opening 48, 148, 248, 348 of non-conductive tube member 46, 146, 246, 346 enables an inert gas, such as argon gas, to pass through non-conductive tube member 46, 146, 246, 346 and over at least a portion of the conductive layer 44, 144, 244, 344 to create an ionized gas (plasma) when the electrode comes into contact with the body/patient thereby creating a closed circuit with a return electrode attached to the body/patient which enables argon beam cutting and/or coagulation with the electrosurgery blade assembly 34, 134, 234, 334.

FIG. 7 is a perspective view of an exemplary embodiment of a monopolar telescopic electrosurgery pencil 400 without argon beam capability which shows the telescopic member 420 disconnected from the handpiece member 412 of the electrosurgery pencil 400 and the interior elements of the electrosurgery pencil 400. FIG. 8 is the same as the view shown in FIG. 7 but with the monopolar telescopic electrosurgery pencil 400 shown rotated 180 degrees and FIG. 9 is an enlarged partial view of FIG. 7.

Monopolar telescopic electrosurgery pencil 400 without argon beam capability includes a handpiece member 412 with a channel 414 having first and second ends 416, 418, a hollow telescopic member 420 having first and second ends 422, 426 where the second end 424 is contained in the handpiece member 412, an electrosurgery blade 433 positioned within the first end 422 of the hollow telescopic member 420 which includes a non-conductive planar member 436 having opposite planar sides 438 with opposing elongated edges 440 and a cutting tip 442, and a conductive layer 444 located on at least one of the opposing planar sides 438 where the conductive layer 444 lies adjacent to at least one of the opposing elongated edges 440 of the non-conductive planar member 436 without covering at least a portion of the opposing planar side 438 that lies adjacent to the cutting tip 442, and a support member 454 for retaining the electrosurgery blade 433 within the hollow telescopic member 420.

In order to make the monopolar telescopic electrosurgery pencil 400 telescopic, the second end 424 of the hollow telescopic member 420 is inserted into the first end 416 of handpiece member 412 so that it is contained within handpiece member 412 when the pencil 210 is in use.

The detailed description of exemplary embodiments of the invention herein shows various exemplary embodiments of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. A monopolar telescopic electrosurgery pencil with argon beam capability, comprising:
   a handpiece member with a channel having first and second ends;
   a first non-conductive hollow tube contained within the channel;
   a conductive hollow tube contained within the channel;
   a hollow telescopic member having first and second ends wherein the second end of the hollow telescopic member is contained within the handpiece member;
   a second non-conductive hollow tube telescopically engaged with the first non-conductive hollow tube wherein the second non-conductive hollow tube is contained within the hollow telescopic member;
   a solid conductive cylindrical member contained within the hollow telescopic member and at least a portion of the conductive hollow tube; and
   an electrosurgery blade assembly positioned within the first end of the hollow telescopic member wherein the electrosurgery blade assembly includes a non-conductive planar member having opposing planar sides with opposing elongated edges and a sharp cutting end, a conductive layer located on at least one side of the opposing planar sides wherein the conductive layer lies adjacent to at least one of the opposing elongated edges of the non-conductive planar member, and a non-conductive tube member having a hollow tubular shaped opening contained therein and a slot contained therein wherein the slot is positioned over at least a portion of the conductive layer and the second non-conductive hollow tube of the monopolar telescopic electrosurgery pencil is connected to the non-conductive tube member of the electrosurgery blade assembly.

2. The monopolar telescopic electrosurgery pencil of claim 1 wherein the slot in the non-conductive tube member is also positioned over at least a portion of the opposing planar sides of the non-conductive planar member of the electrosurgery blade assembly.

3. The monopolar telescopic electrosurgery pencil of claim 1 wherein the hollow tubular shaped opening of the non-conductive tube member is positioned such that an inert gas supplied through the hollow tubular shaped opening will come in contact with at least a portion of the conductive layer of the electrosurgery blade assembly.

4. The monopolar telescopic electrosurgery pencil of claim 1 further comprising at least one support member for retaining the first non-conductive hollow tube and the conductive hollow tube within the channel of the handpiece member.

5. The monopolar telescopic electrosurgery pencil of claim 1 further comprising at least one support member for retaining the second non-conductive hollow tube and the solid conductive cylindrical member within the hollow telescopic member.

6. The monopolar telescopic electrosurgery pencil of claim 1 further comprising a rotating member connected to the second end of the handpiece member.

7. The monopolar telescopic electrosurgery pencil of claim 1 wherein the non-conductive tube member of the electrosurgery blade assembly comprises a ceramic.

8. The monopolar telescopic electrosurgery pencil of claim 1 wherein the non-conductive planar member of the electrosurgery blade assembly comprises a ceramic.

9. The monopolar telescopic electrosurgery pencil of claim 1 wherein at least a portion of the non-conductive tube member of the electrosurgery blade assembly is positioned outside of the first end of the hollow telescopic member.

10. The monopolar telescopic electrosurgery pencil of claim 1 wherein the conductive hollow tube comprises an insulator on its outer surface.

11. The monopolar telescopic electrosurgery pencil of claim 1 wherein the conductive layer of the electrosurgery blade assembly forms a closed loop shaped portion located on one or more of the opposite planar sides of the non-conductive planar member.

12. The monopolar telescopic electrosurgery pencil of claim 11 wherein the conductive layer is on both opposite planar sides of the non-conductive planar member and covers a portion of the opposing elongated edges of each of the opposite planar sides such that it joins the elongated closed loop portions located on each of the opposite planar sides.

13. A monopolar telescopic electrosurgery pencil with argon beam capability comprising:
  a handpiece member with a channel having first and second ends;
  a first non-conductive hollow tube contained within the channel;
  a conductive hollow tube contained within the channel;
  a hollow telescopic member having first and second ends wherein the second end of the hollow telescopic member is contained within the handpiece member;
  a second non-conductive hollow tube telescopically engaged with the first non-conductive hollow tube wherein the second non-conductive hollow tube is contained within the hollow telescopic member;
  a solid conductive cylindrical member telescopically engaged with the conductive hollow tube member wherein the solid conductive tube member is contained within the hollow telescopic member; and
  an electrosurgery blade assembly positioned within the first end of the hollow telescopic member wherein the electrosurgery blade assembly includes a non-conductive planar member having a sharp cutting end, a conductive layer located on the non-conductive planar member, and a non-conductive tube member having a hollow tubular shaped opening contained therein connected to the second non-conductive hollow tube of the monopolar telescopic electrosurgery pencil wherein the hollow tubular shaped opening is positioned over the non-conductive planar member such that an inert gas supplied through the hollow tubular shaped opening will come into contact with the conductive layer on the non-conductive planar member.

14. The monopolar telescopic electrosurgery pencil of claim 13 wherein the diameter of the first non-conductive hollow tube is larger than the diameter of the second non-conductive hollow tube.

15. The monopolar telescopic electrosurgery pencil of claim 14 wherein the diameter of the conductive hollow tube is larger than the diameter of the solid conductive cylindrical member.

16. The monopolar telescopic electrosurgery pencil of claim 13 wherein the diameter of the first non-conductive hollow tube is smaller than the diameter of the second non-conductive hollow tube.

17. The monopolar telescopic electrosurgery pencil of claim 13 further comprising at least one support member for retaining the first non-conductive hollow tube within the channel of the handpiece member.

18. The monopolar telescopic electrosurgery pencil of claim 13 further comprising at least one support member for retaining the second non-conductive hollow tube within the telescopic member.

19. The monopolar telescopic electrosurgery pencil of claim 13 wherein the conductive layer of the electrosurgery blade assembly covers at least a portion of an edge of the non-conductive planar member.

20. The monopolar telescopic electrosurgery pencil of claim 13 wherein the diameter of the conductive hollow tube is larger than the diameter of the solid conductive cylindrical member.

* * * * *